(12) United States Patent
Cook et al.

(10) Patent No.: US 7,175,652 B2
(45) Date of Patent: Feb. 13, 2007

(54) STENT GRAFT WITH IMPROVED PROXIMAL END

(75) Inventors: William A. Cook, Bloomington, IN (US); Thomas A. Osborne, Bloomington, IN (US); Sarah E. Anderson, Cory, IN (US); David E. Hartley, Subiaco (AU)

(73) Assignees: Cook Incorporated, Bloomington, IN (US); William Cook Europe ApS, Bjaeverskov (DK); William A. Cook Australia Pty. Ltd., Queensland (AU)

( * ) Notice: Subject to any disclaimer, the term of this patent is extended or adjusted under 35 U.S.C. 154(b) by 242 days.

(21) Appl. No.: 10/644,129

(22) Filed: Aug. 20, 2003

(65) Prior Publication Data

US 2004/0082989 A1    Apr. 29, 2004

Related U.S. Application Data

(60) Provisional application No. 60/404,662, filed on Aug. 20, 2002.

(51) Int. Cl.
   *A61F 2/06* (2006.01)
(52) U.S. Cl. .................................................. 623/1.13
(58) Field of Classification Search ...... 623/1.13–1.36, 623/2.4–2.41
   See application file for complete search history.

(56) References Cited

U.S. PATENT DOCUMENTS

| | | | |
|---|---|---|---|
| 4,728,328 A * | 3/1988 | Hughes et al. ........... 623/23.69 |
| 5,397,346 A * | 3/1995 | Walker et al. ............. 623/2.41 |
| 5,571,175 A * | 11/1996 | Vanney et al. ............. 623/2.41 |
| 5,843,158 A * | 12/1998 | Lenker et al. ............. 623/1.13 |
| 6,004,347 A * | 12/1999 | McNamara et al. ...... 623/23.64 |
| 6,231,562 B1 * | 5/2001 | Khosravi et al. ........... 604/507 |
| 6,395,019 B2 * | 5/2002 | Chobotov .................. 623/1.13 |
| 6,663,667 B2 * | 12/2003 | Dehdashtian et al. ...... 623/1.51 |
| 6,716,244 B2 * | 4/2004 | Klaco .......................... 623/2.4 |
| 6,846,325 B2 * | 1/2005 | Liddicoat .................... 623/2.4 |
| 2002/0055774 A1 * | 5/2002 | Liddicoat .................... 623/2.4 |

* cited by examiner

*Primary Examiner*—Suzette Gherbi
(74) *Attorney, Agent, or Firm*—Charles W. Agnew (57) ABSTRACT

Disclosed is a stent graft prosthesis comprising a graft portion that includes a main body portion and a cuff portion, the cuff portion generally located at or near the proximal end of the main body portion and extending circumferentially therealong. Stents comprising the graft supporting structure are also attached to graft portion about the proximal end. In one embodiment, the cuff portion comprises material that is folded over the outside surface of the main body portion with an anchoring stent being attached over the cuff and main body portions, extending proximally therefrom. In another series of embodiments, the cuff portion comprises an external sealing zone that extends around the outer main body portion to help prevent leakage of fluids. In one example, the material of the second edge of the cuff portion is frayed to better engage the vessel walls and promote thrombus and/or tissue growth.

16 Claims, 5 Drawing Sheets

STENT GRAFT WITH IMPROVED PROXIMAL END

CROSS-REFERENCE TO RELATED APPLICATIONS

This application claims priority of provisional application Ser. No. 60/404,662 filed Aug. 20, 2002. This application is related to the U.S. patent application Ser. No. 10/322,862 filed Dec. 18, 2002, entitled Stent Graft With Improved Adhesion.

TECHNICAL FIELD

This invention relates to medical devices and more particularly, to intraluminal graft prostheses.

BACKGROUND OF THE INVENTION

The top or proximal edge region of a graft prosthesis, particularly one used to exclude an abdominal aortic aneurysm (AAA) or an aneurysm within the thoracic arch, is that portion of the device which is perhaps most critical to clinical success. Typically, it is the portion of the graft that forms the critical seal against the walls of the aorta to prevent leakage of arterial blood directly into the aneurysmal sac (a situation known as a Type I endoleak). In the case of a stent graft that employs a suprarenal stent or other stent that extends beyond the top edge of the tubular graft, (e.g., the ZENITH® AAA Endovascular Graft, Cook Incorporated), the top edge region also represents the portion to which the stent is sewn or otherwise attached or secured to the graft fabric, typically with a series of sutures. For stent grafts placed in the aorta, the pulsatile forces of blood being exerted on the device are sufficiently great such that over time, the sutures may break or pull through the material, which can cause the anchoring stent and graft to separate. If this occurs, the device may migrate or shift, resulting in the aneurysm no longer being excluded and making a subsequent rupture of the aneurysm potentially lethal to the patient.

While endoleaks can occur anywhere where an aortic stent graft is placed, they can be particularly troublesome when the graft is placed to treat an aneurysm occurring in the region between the renal arteries and the iliac bifurcation. If the neck of the aneurysm (the healthy portion or the vessel between the aneursymal sac and renal arteries) is short or tortuous in shape, it may be difficult to get proper alignment, anchoring, or a good seal between the graft and the vessel wall, possibly resulting in a Type I endoleak in which the sac may continue to be pressurized with blood.

What is needed is an improved proximal edge region of the graft portion of a stent graft prosthesis or covered stent to help ensure secure anchoring of the supporting structure or stent(s) to the fabric or material, and secondly, to ensure a good seal with the vessel wall such that leakage of blood or fluids does not occur along the proximal edge of the prosthesis.

SUMMARY OF THE INVENTION

The foregoing problems are solved and a technical advance is achieved in an illustrative intraluminal prosthesis, such as a stent graft, made of a sleeve of material (e.g., a tight-mesh fabric, extruded polymer, and/or a biomaterial) which includes a leading edge portion having an external structure configured to prevent anchoring stent detachment and/or leakage of blood or fluids around the graft portion. In one aspect of the invention, the stent graft includes a proximal cuff portion to which at least the proximal stent may be attached, thereby providing at least a first and second layer of material that helps provide a more secure substrate for the attached stent(s). The double layer is more likely to hold the sutures and keep them intact, as well as being less likely to have a portion of the stent wear through the fabric over time. A first illustrative embodiment comprises a stent graft adapted for use in treating an aortic aneurysm, such as the ZENITH® AAA Endovascular Graft, in which the most proximal stent extends beyond the proximal or top edge of the graft potion to help anchor the stent graft in the vessel. The prosthesis is placed at or above the iliac bifurcation with the proximal stent acting as a suprarenal stent, attaching to the healthy portion of the aorta about and above the openings to the renal arteries. Because this particular stent typically is only attached about the distal bends and strut portions, there are relatively few sutures to anchor the stent to the material. The cuff of the present invention gives a double-thickness layer of graft material, such as DACRON® polyester fiber (trademark of EI duPont de Nemours & Co., Inc.) for holding the sutures intact and providing better assurance that the distal bends or struts of the zig-zag stent will not wear through the fabric, creating a hole or causing detachment of the suprarenal stent at that point.

The stent adjacent to the proximal anchoring (suprarenal) stent may also be partially attached to the cuff as well. The proximal stent can be sewn to the cuff from the inside or the outside of the graft, preferably, but not necessarily to both the main body and cuff portions. Additionally, the stent can be sewn to the graft material's folded or leading edge such that the stent and graft material generally abut one another. This reduces thickness by not having the struts of the stent overlapping the material. Furthermore, the cuff can comprise a separate piece of the same or a different material that is sewn, bonded, applied, or otherwise attached to the main body of the graft with the anchoring stent or other supporting structure being attached to both layers to provide added support. While the cuff preferably encircles the entire circumference of the main body of the graft, it is within the scope of the invention (and definition of the term 'cuff') to include a series of discrete cuff 'flaps' or patch-like elements distributed around the circumference of the main body as points to which the bends or struts of the anchoring stent or other supporting structure are attached.

In one embodiment, at least a portion of the proximal stent is attached to the graft between the layers of the cuff to further strengthen the stent-graft attachment by having the folded edge provide a stop to prevent the stent, which may be inserted through holes about the folded edge, from pulling through if becoming detached from the fabric. Although the folded first edge of the cuff may provide a better substrate for preventing sutures pulling out as compared to a cut edge of material, it is within the scope of the invention to include a cuff in which both the first edge of the cuff and the first end of the main graft body comprise free or cut edges of fabric or other material, rather than a folded edge to unite them.

In another aspect of the invention, the cuff, which comprises a first edge at the leading or folded edge of the graft extending to second edge that comprises the free or cut edge of the material, is adapted to extend outward to serve as an external sealing zone to engage the vessel wall and help prevent leakage of blood or fluid around the device. In one illustrative embodiment of a modified ZENITH® AAA Endovascular Graft, approximately 10 mm of the graft material is folded over on itself such that the free edge is on the outside of the graft. Approximately the distal 5 cm of the cuff includes a region in which the threads and fibers of the DACRON® polyester fabric have been at least partially separated from one another to create a frayed region that extends outward from the graft and facilitates sealing by encouraging thrombus formation and tissue ingrowth. Graft material, such as DACRON® polyester fiber, is particularly well-suited to form thrombus. One advantage of the external sealing zone is that the top or first supporting stent, which has the ability to compromise the quality of the graft-vessel seal if placed on the outside of the graft (such as is the case with the ZENITH® AAA Endovascular Graft), can be moved from the inside to the outside of the graft and still allow for adequate sealing. This allows the inner lumen of the graft to remain smooth and stent-free. In a variation of this embodiment, the frayed region is folded or otherwise directed so that it extends proximally, thereby creating a third layer of graft material along the first edge of the cuff. Additionally, the frayed region can be modified to enhance its sealing properties, such as by adding agents to encourage thrombosis or cell proliferation, adding structure capable of stimulating the cell injury response and facilitate tissue ingrowth.

In yet another aspect of the invention, the external sealing zone can include separate element or series of elements that includes the same material and/or a second material which is affixed to the outer surface of the graft. It can be attached to or below the cuff, or the cuff can be eliminated completely. Some examples of materials for an attached external sealing zone include bands of felt material, foam, lyophilized collagen, such as small intestinal submucosa (SIS) or another extracellular matrix (ECM), or some other suitable material.

BRIEF DESCRIPTION OF THE DRAWINGS

Embodiments of the present invention will now be described by way of example with reference to the accompanying drawings, in which.

DETAILED DESCRIPTION

Figure 1:
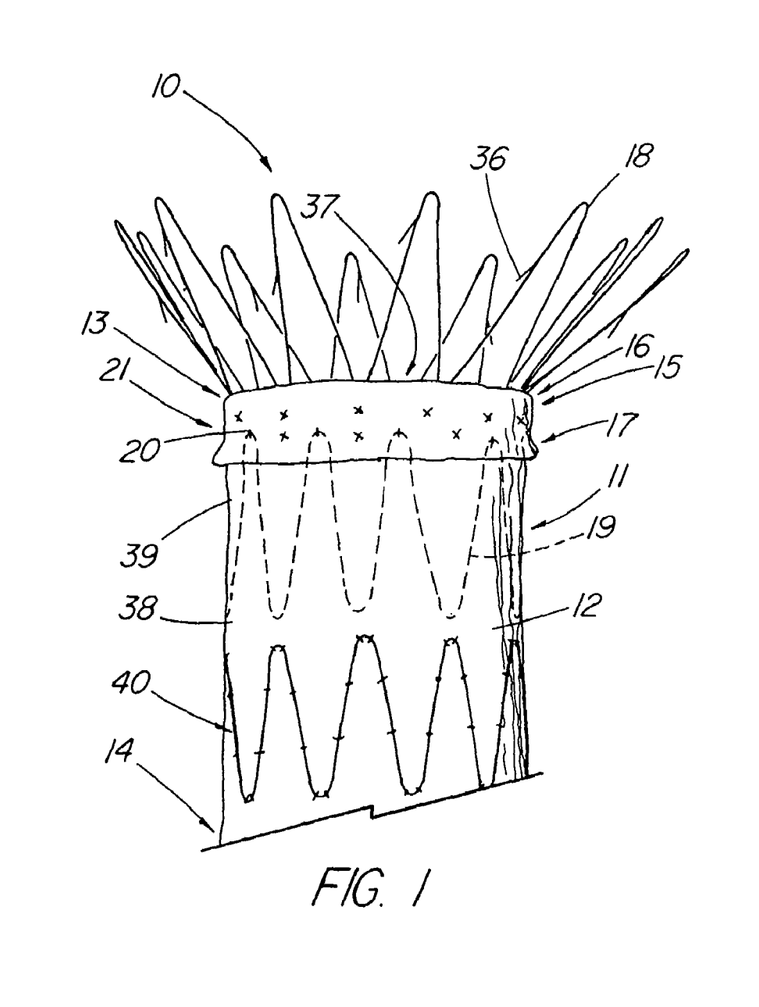
FIG. 1 depicts a side view of an illustrative embodiment of the present invention in which the graft portion includes a proximal cuff portion.

FIG. 1 depicts a graft prosthesis 10 that includes a graft portion 11 having a first end 13, which typically forms the proximal or leading edge of the main body 12 of the tubular graft portion, and a second end 14, which typically is the distal end which is further downstream from the direction of blood or fluid flow. The illustrative graft prosthesis 10 represents a modified ZENITH® AAA Endovascular Graft comprising a tubular graft portion 11 of DACRON® polyester fiber (including a bifurcated distal portion in this embodiment to feed into the right and left iliac arteries), and a supporting structure 40 that comprises a series of zig-zag stents sewn thereto, including a proximal anchoring stent 18, such as the illustrative suprarenal zig-zag stent with barbs, extending from the proximal (caudal) end to anchor the stent graft above the aneurysmal sac. The prosthesis 10 further includes a cuff portion 15 comprising material of the main body 12 that is folded over the outside thereof to form a double layer of material. The cuff portion 15 includes a first edge 16 or leading edge, which is typically a folded edge, that also comprises the first end 13 of the graft portion 11, and extends distally to a second edge 17, which is the free edge of the cuff. In the illustrative cuff portion 15, the free edge 17 is unattached to the main body 12 so that it is allowed to extend or flair outward to comprise a lip that serves as an external sealing zone 21 to help provide a better seal graft portion 11 and walls of the vessel in which the device is placed. It should be noted that while it may be preferable to form the cuff portion 15 by folding the excess material over upon itself, it is also within the scope of the invention for the cuff portion 15 to be a separate piece that is secured to the main body 12 of the graft portion, such that the proximal edges of the main body and cuff portions 13,16 each comprise 'cut' or free edges rather than a single folded edge. The double thickness of the cuff portion typically offers a better foundational substrate through which sutures 20 may be attached, forming knots to secure or anchor stents or other framework of the graft prosthesis 10. The length of the cuff 15 depends largely on the specific clinical application and size of the prosthesis, but preferably the free edge 17 does not extend more than a few centimeters from the first end 13, especially in an endovascular stent graft where the seal must be safely proximal of the aneurysm being excluded. The cuff portion 15, however, may extend any length, including the entire length of the main body portion 12, particularly if it is not utilized as an external sealing zone 21. Although it is generally preferred that the cuff be folded or placed over the outer surface of the main body portion 12 so as not to interfere with blood flood and promote formation of thrombus, it may folded inward and attached, particularly if the free edge 17 can be attached or bonded in such a manner that does not interrupt blood flow.

Figures 12, 13, 14:
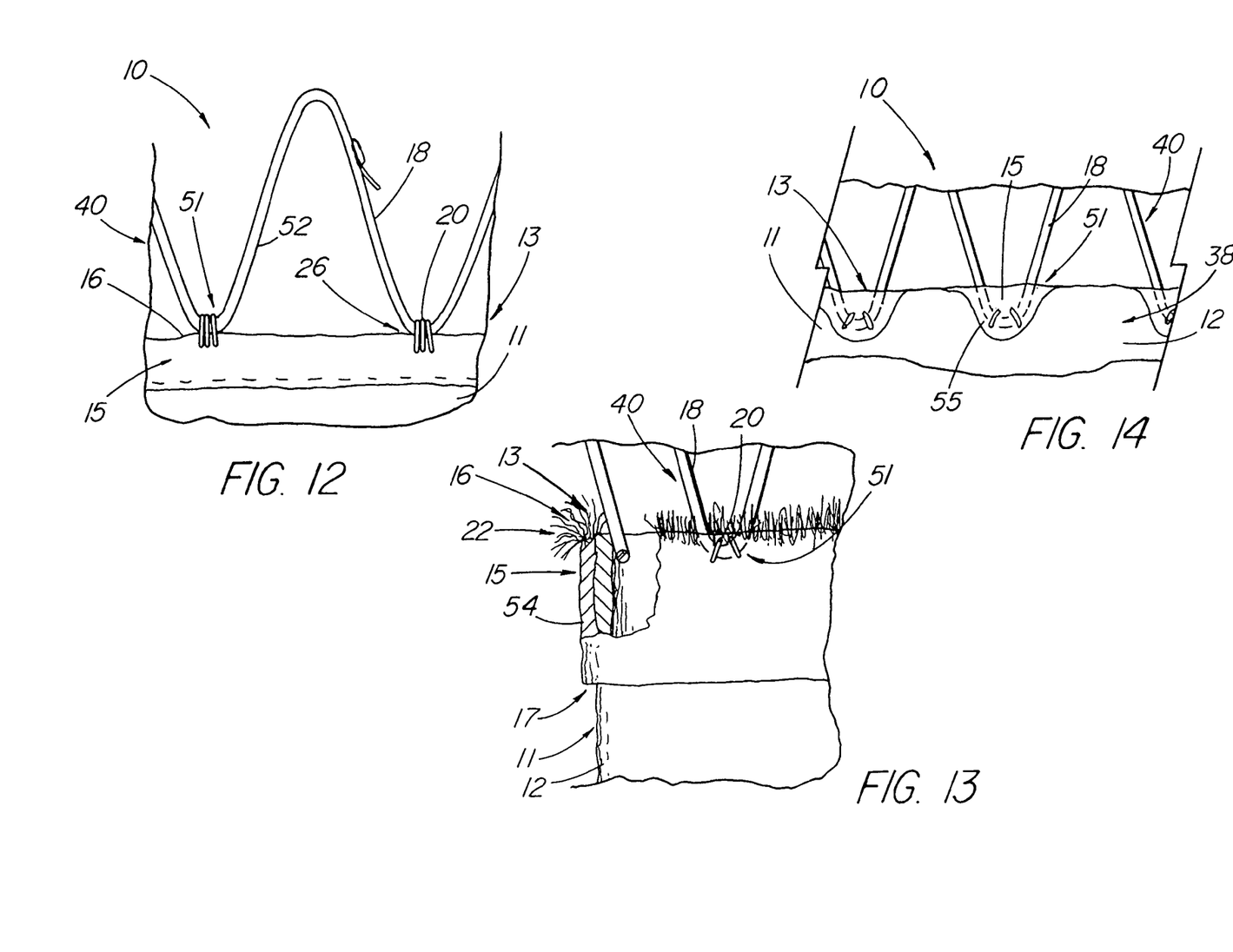
FIG. 12 depicts an enlarged side view of an alternative embodiment in which the proximal anchoring stent is attached about the edge comprising the first end of the graft material.
FIG. 13 depicts a partially sectioned side view of an alternative embodiment in which the cuff portion comprises a layer of material separate to the main body portion of the graft.
FIG. 14 depicts a side of an embodiment in which the cuff portion comprises a plurality of flaps.

FIG. 14 depicts an alternative embodiment of the cuff portion 15 in which the cuff is configured as a series of discontinuous flaps 55 distributed around the outer perimeter of the main body portion 12 of the graft. The flaps 55 are spaced to correspond to the attachment points of the bends 51 of the anchoring stent 18. Although the illustrative embodiments each depict a suprarenal anchoring stent 18, it is not necessary to the invention that the supporting structure 40 attached to the cuff 15 comprise an anchoring stent extending from the proximal end 13 of the graft 11.

The illustrative ZENITH® AAA Endovascular Graft represents but one exemplary embodiment of the present invention. As such, the stent graft material 11 and supporting structure 40 may include other well-known materials and designs. For example, other biocompatible fabrics and non-woven materials, such as expanded polytetrafluoroethylene (ePTFE) may be used as well as biomaterials, such as cross-linked collagen and remodelable collagen materials, e.g, a tube formed from a single or multiple ply tube of a extracellular collagen matrix material (SIS being an example commercially available from Cook Biotech, Inc., West Lafayette, Ind.).

The suture 20 used to attached supporting structure 40 to the graft material 11 may be made of any biocompatible fiber suitable for the application, including but not limited to, monofilament or braided multi-filament polyester, nylon, polyaramid, polypropylene, and polyethylene. Braided polyester 4-0 suture material is preferred for attaching internal stents to grafts, while monofilament suture material is preferred for attaching top stents to grafts. The polyester 4-0 suture material is nonabsorbable and has limits of 0.150 to 0.199 mm (metric size 1.5). This well-known material is commercially available from a number of companies. The suture material may be attached to a hollow needle used to thread the suture through the graft, thus attaching the stent to the graft using any suitable type of knot. It is not necessary to the invention that fiber suture be used to attach the supporting structure to the graft material. Wire, staples, clips, bonding agents, or other methods also may be used to achieve a secure attachment of the graft material and stents.

Figure 2:
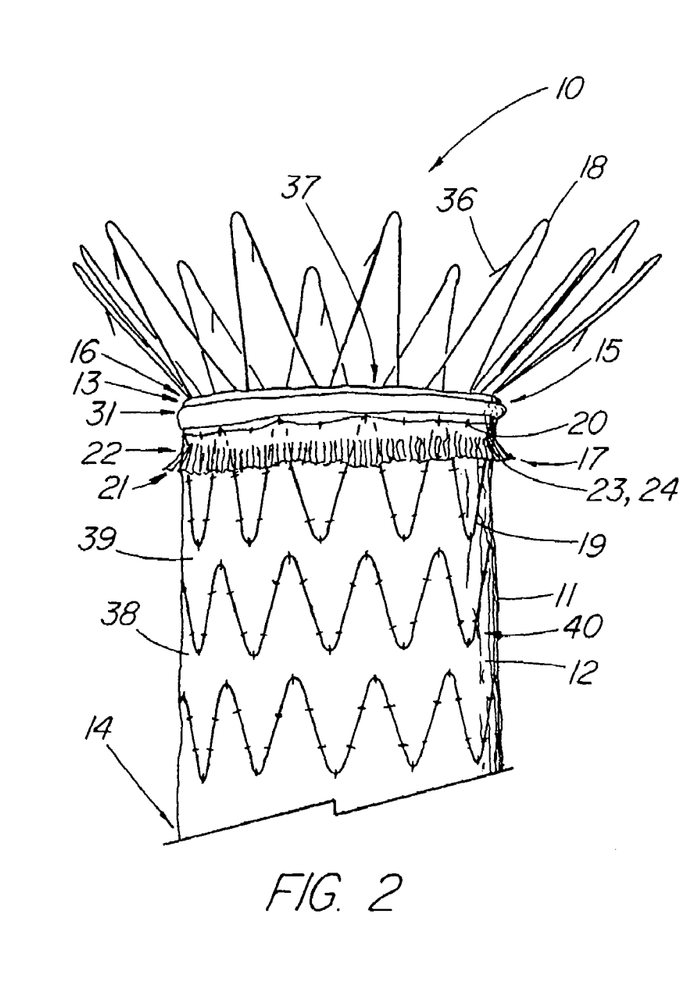
FIG. 2 depicts a side view of an embodiment of the present invention where the cuff portion includes an external sealing zone comprising a frayed portion.
Figure 3:
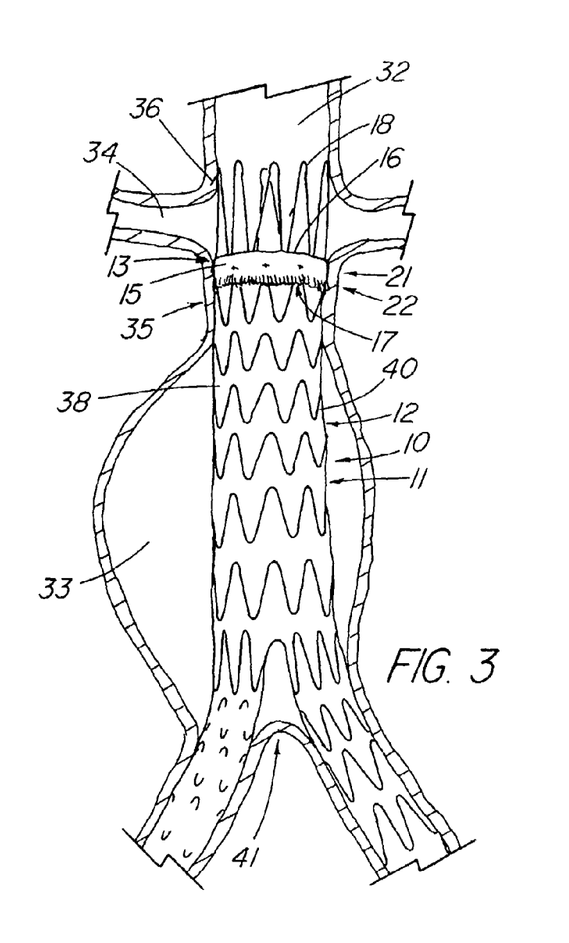
FIG. 3 depicts an in situ view of the embodiment of FIG. 2.

To further enhance the sealing properties of the external sealing zone 21, the free edge may be modified to increase its ability to conform with the vessel, promote thrombus formation, and/or encourage tissue ingrowth into the graft material. FIG. 2 depicts an embodiment of the present invention in which the cuff 15 includes a frayed portion 22 located about the free end 17 thereof, the frayed portion 22 comprising about 5 mm of threads and fibers (of an approximately 10 mm cuff) that have been at least partially separated from one another or unraveled such that they extend outward from the main graft body 12 and circumferentially therearound. Alternatively, the frayed portion 22 may extend the entire length of the cuff portion 15. The frayed portion 22 is particularly well adapted to make contact with the vessel and allow thrombocytes to collect and tissue to grow thereinto, thus improving the efficacy of the seal. FIG. 3 depicts the illustrative embodiment of FIG. 2 deployed in an abdominal aorta 32 to exclude an aneurysm 33 that has formed below the renal arteries 34, usually above or at the iliac bifurcation 41. The external sealing zone 21 comprising the frayed portion 22 is positioned within the neck 35 of the aneurysm 33 where it helps the stent graft 10 seal against the healthy aortic wall tissue so that an endoleak does not occur around the proximal end 16 of the graft. The proximal anchoring stent 18 is placed across the renal arteries where it is anchored to the vessel 32 by a plurality of barbs 36. In other embodiments, the proximal anchoring stent 18 may include hooks or other structure that extend beyond or through the graft material 38 to engage the vessel and help anchor the prosthesis in place.

Figure 4:
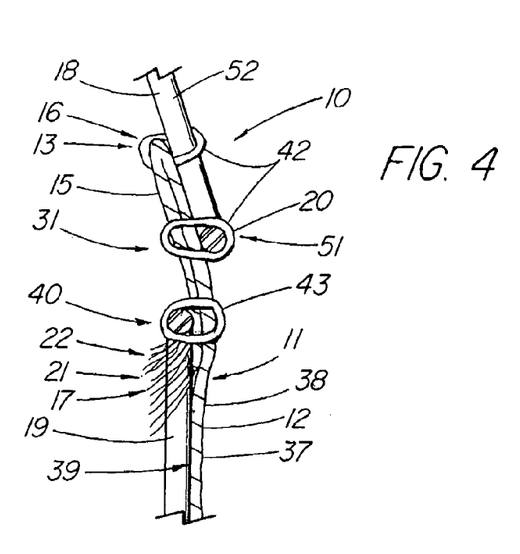
FIG. 4 depicts a cross-sectioned view of the cuff of FIG. 2.

FIG. 4 depicts a cross-sectional view taken about the proximal end 16 of the graft portion 11, including the cuff portion 15 and proximal anchoring stent 18. The proximal anchoring stent 18 is attached to the inner surface 37 of the graft material 38 and secured with sutures 20 that are passed through both the main graft body 12 (inner) and the cuff portion 15 (outer) layers of material 38, preferably through the proximal or anchoring portion 31 of the cuff portion 15. In particular, a series of interconnecting (running) or separate sutures 42 anchor the proximal anchoring stent 18 to the cuff portion 15 at the bends 51 and struts 52 of the stent 18, the later being sutured about the proximal or folded edge 16 of the cuff. Additionally, the first adjacent supporting stent 19 is attached to the outer surface 39 of the main graft body 12 with a another series of sutures 43. The illustrative example depicts the frayed portion 22 extending through and around the struts to minimize direct contact of the stent with the vessel wall, thus resulting in a better seal than would otherwise be possible with an externally placed stent.

Figure 11:
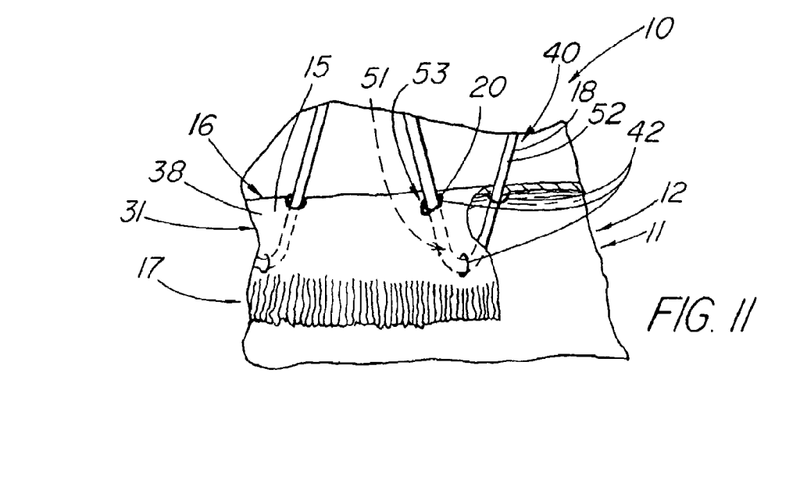
FIG. 11 depicts a partially sectioned detail view of an alternative embodiment in which the proximal anchoring stent is attached underneath the cuff portion.

FIG. 11 depicts an alternative embodiment of the present invention in which the proximal anchoring stent 18 is attached to the graft portion 11 between the main body 12 and cuff portion 15, such that the bends 51 and distal portions of the struts 52 being sandwiched between graft material 38, providing a more secure anchoring of the stent. One skilled in the medical arts would appreciate that there are multiple methods of forming the embodiment of FIG. 11. One method is to feed an end of an unassembled proximal anchoring stent through a series of holes 53 formed through the graft material until all of the bends 51 are looped underneath the cuff portion 15, as shown. The stent 18 is then joined together with cannula and solder, spot or laser welding, etc., and secured with a series of sutures 42. The illustrative method of attachment provides a backup means of preventing the proximal anchoring stent 18 from completely detaching from the graft portion 11 in the event of suture 20 failure.

FIG. 12 depicts an embodiment in which the proximal anchoring stent 18 is attached at the proximal (folded) edge 16 of the cuff portion 15 by a plurality of sutures 20 (either multiple sutures or multiple loops of a single suture) such that no portion of the bends 51 or struts overlaps with the stent graft material 11. This advantageously reduces the profile of the graft prosthesis 10 during the loading process.

While the cuff portion 15 of the illustrative embodiments is shown as a free edge 17 that is folded over itself (the tubular prosthesis 12) to create a double thickness of material (new folded leading edge 16), it is within the scope of the invention for the cuff portion to be a separate element that is attached to the main body 12 of the graft (FIG. 13), such as when the sutures 20 penetrated both layers to attach the anchoring stent 18 or other supporting structure 40. Adhesives, laser/thermal bonding, or other methods may be used supplement or achieve attachment of the two layers of material 12,15. The separate ring-like outer cuff portion 54 comprising the outer portion of the cuff 15 may be of the same material of the main body 12, or a different material, particularly one having advantageous properties such as better durability, thinner profile, remodelability/tissue ingrowth facilitation (e.g., an ECM), or superiorability to elute medicaments or agents, etc., without regard to whether the second material is particularly suitable to prevent the leakage of blood therethrough. Furthermore, the separate outer cuff portion 54 can comprise a material, such as a polymer, that is printed, sprayed, painted, dipped, or otherwise applied to the surface of the graft prosthesis to improve the attachment between stent and graft material. The illustrative embodiment of FIG. 13 further includes a frayed portion 22 located at the leading edge 16 of the cuff portion 15 to facilitate sealing thereat. Alternatively, the optional frayed portion 22 may be located at the second edge 17 of the cuff 15, similar to the embodiment of FIG. 2, or it may be located at the first edge 13 of the main body 12, or any combination of the three free edges 13,16,17. By being separate pieces, the outer cuff portion 54 and main body may be used to form a sandwich of material to secure the anchoring stent 18 therebetween (not shown), similar to the embodiment of FIG. 11. Although the illustrative separate outer cuff 54 completely encircles the main body 12 to which it is attached, it may be divided into discrete sections that are located at the attachment points of the stent bends 51 to provide a double thickness of material.

Figure 5:
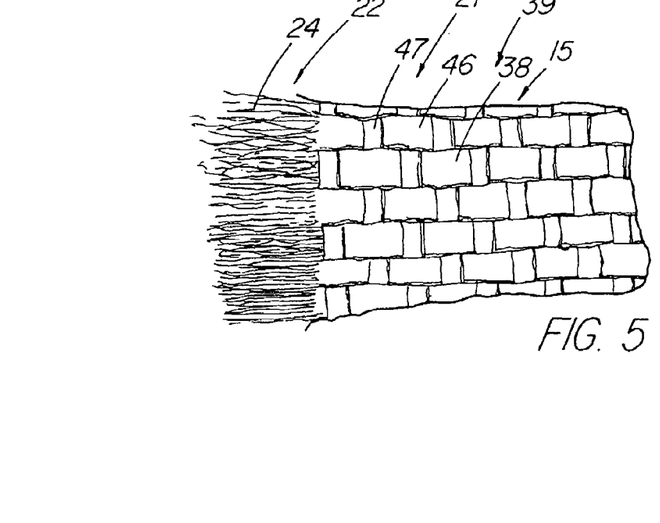
FIG. 5 depicts a detailed view of the free edge of the cuff portion of FIG. 2.

FIG. 5 depicts an enlarged view of the frayed portion 22 and how it is formed from material 38 of the cuff portion 15. The illustrative TWILLWEAVE™ graft material 38 (Selzer-Vascutek Ltd., Inchinnan, Scotland, UK) comprises a woven DACRON® polyester fabric which is frayed by separating the longitudinal threads 46 from one another and from the cross threads 47 with which they are interwoven. Once the ends 23 of the threads 46 are separated, typically using a tool or machine suitable for creating a frayed portion 22 of the desired length, the fibers 24 that comprise the individual longitudinal threads 46 are preferably, but not necessarily, also unraveled and separated from one another, allowing the frayed portion 22 to assume a 'fuzzier' configuration that enhances the sealing properties of the external sealing zone 21 and provides an improved substrate for tissue ingrowth thereinto. Generally, it is preferred that the portion in which the fibers 24 are separated from one another, comprises at least a substantial portion of the frayed portion 22. The length of frayed portion 22 of a typical stent graft comprises at least 2 cm of the cuff portion 15 (preferably 5 mm or more).

Figure 6:
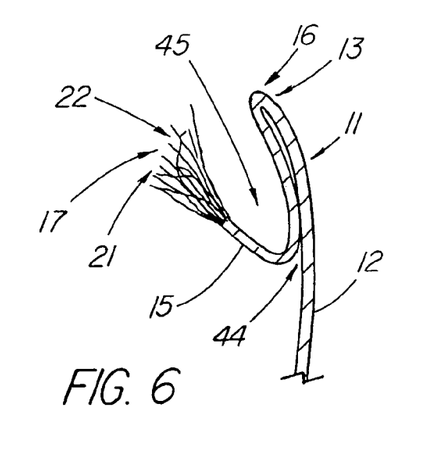
FIG. 6 depicts a cross-sectional embodiment of the present invention wherein the free edge of the cuff portion is directed toward the first end of the graft.

FIG. 6 depicts an embodiment in which the external sealing zone 21, including the illustrative frayed portion 22, is configured such that the free edge 17 of the cuff portion 15 is directed proximally (toward the first or folded edge 16), to produce a fold 44 that creates gutter-like pocket 45 that is able to collect any blood passing around the leading edge 16 of the graft 11 to prevent an endoleak and promote thrombus formation. The pocket 45 can be created by any means known to those in the medical arts, including treating and forming the cuff material using a chemical agent, heat, etc. such that it can maintain such a shape; or by adding wires or other supporting structure (not shown) that reshapes the cuff portion 15 into the illustrative pocket 45 configuration.

Figure 7:
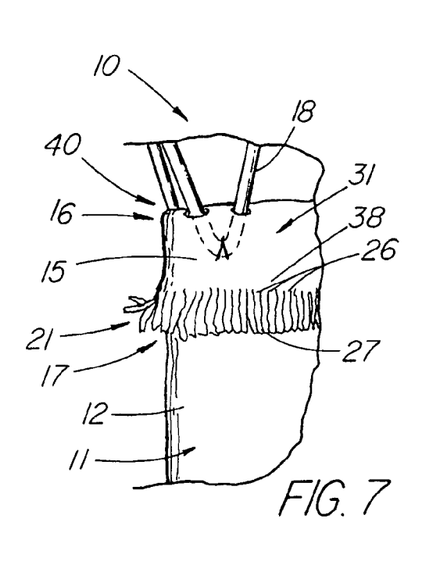
FIG. 7 depicts a detail view of an alternative cuff embodiment wherein a fringe is cut into the free edge of the graft material.

Although DACRON® polyester fiber and other selected fabrics usable in medical applications are generally able to be unraveled to create a frayed portion 22, some fabrics and unwoven materials potentially suitable for medical applications, such as polymer sleeves, biomaterials, etc., cannot be frayed in the same manner. FIG. 7 depicts an external sealing zone 21 created by creating a series of closely adjacent cuts 26 or slices through the material to form fringe elements 27 about the free edge 17 of the material. The length, width, and configuration of the fringe elements 27 (fringed portion) are largely determined by the clinical application and type of material 38 comprising the cuff portion 15.

Figure 8:
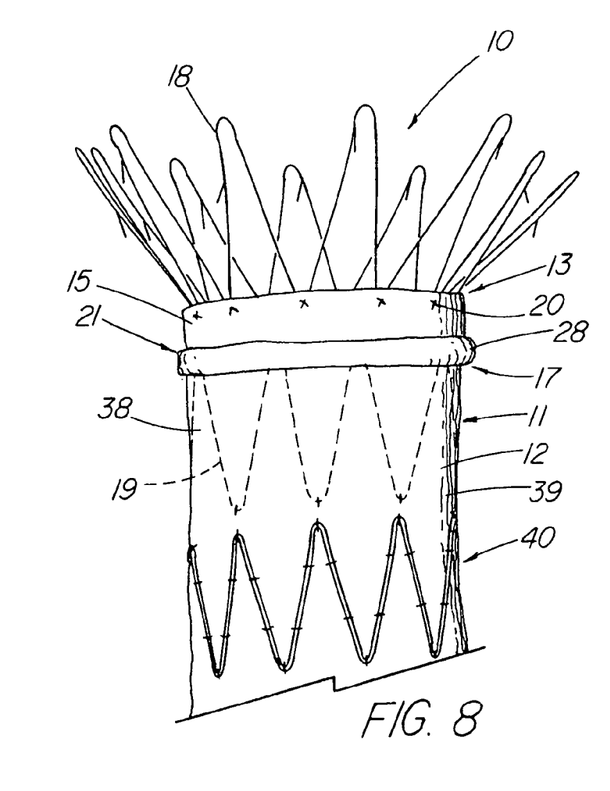
FIG. 8 depicts an alternative embodiment of the present invention wherein the external sealing zone comprises a band of material attached to the graft.

In addition to the external sealing zone 21 comprising the free edge 17 of the cuff portion 15, as with each of the embodiments described above, FIG. 8 depicts an embodiment wherein the external sealing zone 21 comprises a band 28 of separate material such as open-cell foam or another suitable biocompatible material (e.g., a lyophilized or sponge-form collagen material such as SIS) and configuration which is attached to the outer surface 39 of the graft. Such materials should be effective for creating a seal with vessel wall and/or encouraging cell ingrowth. Such a band of material 28 can be affixed over the cuff portion 15, such as over the free edge 17, as shown, attached below the cuff 15 to further take advantage of the free edge 17 for sealing, or the cuff portion 15 may be eliminated entirely if not needed for additional anchoring support. While the illustrative embodiments depicts an external sealing zone 21/frayed portion 22 that encircles the graft 11 in a ring-like manner, it may assume other configurations, such as a helically or serpentine shaped strips of material, discrete staggered patches of material/fringe, etc.

Figure 9:
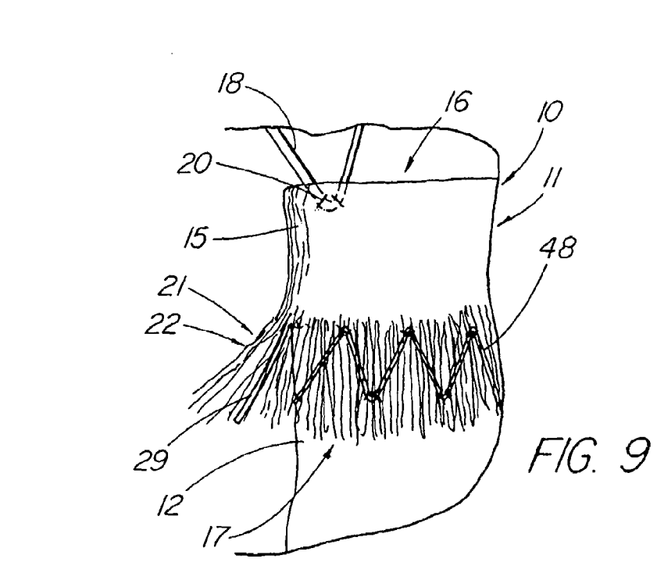
FIG. 9 depicts an alternative embodiment of the present invention in which the frayed portion includes additional structure to promote thrombus formation and/or tissue ingrowth.

The external sealing zone 21 may be augmented with additional structure, materials, or agents that further enhance its sealing properties. One example includes tissue-engaging elements 29, such as the illustrative barbs depicted in FIG. 9. The barbs 29 may be configured to help anchor the graft prosthesis 10 in the vessel, or their primary function may be limited to providing irritation or trauma to the vessel wall for stimulating cell proliferation into the external sealing zone 21. The tissue engaging elements 29 may comprise any suitable structure, such as a plurality of small diameter wires, which are interwoven into the cuff portion 15, or attached in any suitable manner, such as the illustrative method in which the barbs 29 originate from a common basal element 48 that encircles the graft portion 11 and is design to be collapsible (e.g., a zig-zag shaped element). The tissue-engaging elements 29 may also configured to bias the cuff portion toward the wall during delivery (e.g., by adding springs or other biasing mechanisms about the common basal element 48). For example, the prosthesis 10 may be loaded such that the cuff portion could be loaded such it extends proximally from the main body portion 12. As the graft prosthesis is unsheathed for delivery, the embedded elements 29 spring back and flip the cuff portion distally to engage the walls of the vessel. This has the advantage of eliminating the extra thickness of the cuff portion 15 during loading, yet retaining the advantages it provides following deployment.

Besides tissue-engaging structures 29, the external sealing zone 21 may be impregnated with a bioactive or pharmacological agent that enhances sealing properties, such as thrombin powder or another agent for stimulating thrombus formation about the external sealing zone 21. Other possible materials or agents, include, but are not limited to, growth factors or biomaterials for stimulating tissue ingrowth, materials that swell in the presence of blood, or other substances that help form a physical barrier to fluids.

Figure 10:
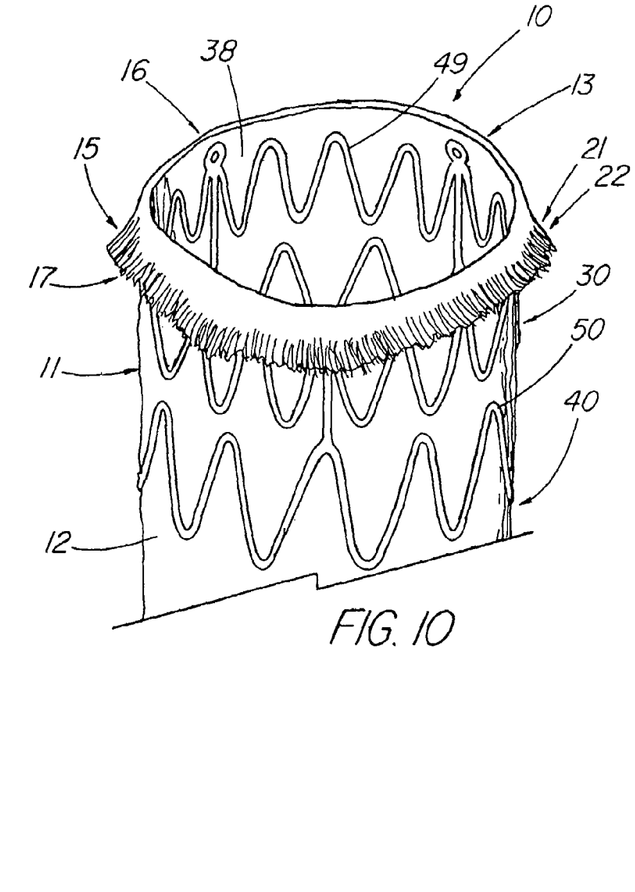
FIG. 10 depicts an alternative embodiment of the present invention wherein the cuff portion comprises a portion of the graft material extending over the leading edge of a cannula stent.

FIG. 10 depicts an embodiment of the present invention in which the cuff portion 15 extends beyond and over a self-expanding or balloon-expandable outer stent 50 and whose function is primarily to serve as an external sealing zone 21, rather than also being a substrate for attachment of a proximal anchoring stent or other supporting structure 40. In the illustrative example, which depicts a cannula-type stent 30, such as the illustrative ZILVER® Stent (Cook Incorporated), the cuff portion 15 comprising the frayed portion 22, extends a few millimeters beyond the proximal or first end 13 of the stent and is unattached to the stent 50, although it optionally might include a series of sutures above the frayed portion 22 to maintain a folded edge 16 and prevent the cuff portion from inverting. In the illustrative example, the prosthesis 10 includes an inner stent 49 to form a sandwich configuration in which the two stents 49,50, one expanding slightly larger than the other, engage and maintain the graft material 38 therebetween, thereby eliminating the need for suturing the graft portion 11 to the supporting structure 40. It is certainly within the scope of the invention, however, for either stent to be eliminated and have the graft material sewn or otherwise attached to the stent supporting structure 40 in a manner similar to other depicted embodiments. Additionally, other types of cannula or non-cannula stents can be substituted for the illustrative stents 49,50, which need not be the same as one another.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention. The invention encompasses embodiments both comprising and consisting of the elements described with reference to the illustrative embodiments. Unless otherwise indicated, all ordinary words and terms used herein shall take their customary meaning as defined in The New Shorter Oxford English Dictionary, 1993 edition. All technical terms shall take on their customary meaning as established by the appropriate technical discipline utilized by those normally skilled in that particular art area. All medical terms shall take their meaning as defined by Stedman's Medical Dictionary, 27$^{th}$ edition.

What is claimed is:

1. A stent graft prosthesis for placement in a vessel comprising:
   a graft portion including a first end, a second end, and a main body portion, generally tubular in shape, that comprises a first layer of material;
   a cuff portion, having a first edge and a second edge, the first edge thereof located about the first end of the main body of the graft portion, the cuff portion comprising a second layer of material closely adjacent the main body portion wherein the second edge comprises one of a frayed portion and a fringed portion; and
   a supporting structure attached about the first end of the graft portion and to the cuff portion.

2. The stent graft prosthesis of claim 1, wherein the cuff portion is folded over the main body portion such that the proximal, first end of the cuff portion comprises a folded edge and the second end comprises a free edge.

3. The stent graft prosthesis of claim 2, wherein the cuff portion is folded over the outside of the main body portion.

4. The stent graft prosthesis of claim 3, wherein the cuff portion comprises a plurality of flaps extend over the first edge of the graft portion.

5. The stent graft prosthesis of claim 1, wherein the supporting structure includes an anchoring stent attached to the cuff portion and main body portion.

6. The stent graft prosthesis of claim 1, wherein the cuff portion comprises one or more elements separate of the main body portion that are attached thereto.

7. The stent graft prosthesis of claim 6, wherein the cuff portion comprises an external sealing zone extending laterally from the main body portion, the external sealing zone configured to engage the walls of the vessel to facilitate sealing therebetween and reduce leakage of fluid.

8. The stent graft prosthesis of claim 1, wherein the cuff portion comprises a second material different than that of the main body material.

9. A stent graft prosthesis for placement in a vessel comprising:
   a graft portion including a main body portion generally tubular in shape, that includes a first end and a second end;
   a cuff portion comprising an external sealing zone generally located at or closely adjacent the first end of the graft portion, the external sealing zone having structure comprising a second layer of material that generally encircles and extends laterally from the main body portion to create a circumferential seal between graft portion and the adjacent walls of the vessel to reduce leakage of bodily fluid thereabout; and
   wherein the cuff portion comprises a band of material situated therearound.

10. The stent graft prosthesis of claim 9, wherein the cuff portion comprises a frayed portion.

11. The stent graft prosthesis of claim 9, wherein the cuff portion comprises a fringed portion.

12. The stent graft prosthesis of claim 9, wherein the band of material comprises a second material, wherein the second material is different than that of the main body of the graft portion.

13. A stent graft prosthesis for placement in a vessel comprising:
   a graft portion including a main body portion;
   an outer cuff portion, having a first edge and a second edge, that is located about the first end of the graft portion and attached thereto wherein the outer cuff portion comprises a frayed portion; and
   an anchoring stent attached to the main body portion and outer cuff portion, the anchoring stent extending proximally therefrom.

14. The stent graft prosthesis of claim 13, wherein the outer cuff portion comprises an external sealing zone.

15. The stent graft prosthesis of claim 13, wherein the outer cuff portion is folded over the main body portion with the anchoring stent being attached thereover.

16. The stent graft prosthesis of claim 13, wherein the outer cuff portion is folded over the main body portion with the anchoring stent being attached between the outer cuff portion and the main body portion.

* * * * *